United States Patent [19]

Maass

[11] 4,076,839
[45] Feb. 28, 1978

[54] URICOSURIC COMPOSITION AND METHOD OF PRODUCING URICOSURIA AND HYPOURICEMIA

[75] Inventor: Alfred Roland Maass, Swarthmore, Pa.

[73] Assignee: SmithKline Corporation, Philadelphia, Pa.

[21] Appl. No.: 810,244

[22] Filed: Jun. 27, 1977

[51] Int. Cl.² .............................................. A61K 31/19
[52] U.S. Cl. ..................................................... 424/317
[58] Field of Search ......................................... 424/317

[56] References Cited

PUBLICATIONS

Tarbell, et al., J. Am. Chem. Soc., vol. 64, (1942), pp. 1066–1070.
Tarbell, et al., J. Am. Chem. Soc., vol. 64, (1942), pp. 607–6112.
Chem. Abst., vol. 41, (1947), p. 3905e.
Chem. Abst. Chem. Substance Index, vol. 83, (1975), p. 4569cs.

*Primary Examiner*—Sam Rosen
*Attorney, Agent, or Firm*—Richard D. Foggio; William H. Edgerton

[57] ABSTRACT

Uricosuric compositions containing 2,3-dichloro-4-carboxyphenoxyacetic acid or its alkali metal salts and methods of producing uricosuria and hypouricemia by administering said compounds.

9 Claims, No Drawings

URICOSURIC COMPOSITION AND METHOD OF PRODUCING URICOSURIA AND HYPOURICEMIA

This invention relates to novel uricosuric compositions containing an active ingredient which increases urinary excretion and clearance of uric acid, and to a method of producing uricosuria and hypouricemia by administering nontoxic effective quantities of said ingredient to a subject in need thereof. More specifically, the active ingredient used in the compositions and methods of this invention is 2,3-dichloro-4-carboxyphenoxyacetic acid which has the following formula:

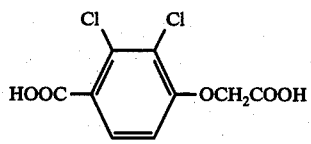

FORMULA I or an alkali metal salt of said acid, for example the sodium or potassium salt.

The acid of formula I is conveniently prepared from 2,3-dichloro-4-hydroxybenzoic acid by reaction with sodium monochloroacetate in the presence of sodium hydroxide or with ethyl chloroacetate following by hydrolysis with for example, potassium hydroxide, to give the diacid. The 2,3-dichloro-4-hydroxybenzoic acid is obtained by reaction of 2,3-dichlorophenol with carbon tetrachloride under Riemer-Tiemann conditions. Details of these preparations are given in the Examples below.

Isomers of the compound of formula I are known, namely 2,6-dichloro-4-carboxyphenoxyacetic acid (J. Am. Chem. Soc. 64:1066–70, 1942) and 2,4-dichloro-6-carboxyphenoxyacetic acid (J. Am. Chem. Soc. 64:607–12, 1942). The latter isomer is described as a plant growth inhibitor (C.A. 41:3905$^e$).

The uricosuric activity of 2,3-dichloro-4-carboxyphenoxyacetic acid or its alkali metal salts is determined by intravenous administration to the phosphate-mannitol infused mongrel dog. From renal clearance studies the effect of the test compound on uric acid excretion is determined. In this study, 2,3-dichloro-4-carboxyphenoxyacetic acid at a dose of 60 mg/kg i.v. increased uric acid filtered by 116%.

The uricosuric compositions of this invention are prepared in conventional dosage unit forms by incorporating 2,3-dichloro-4-carboxyphenoxyacetic acid or pharmaceutically acceptable salt thereof, in a nontoxic amount sufficient to produce uricosuria and hypouricemia in a designated subject, with a nontoxic pharmaceutical carrier according to accepted procedures. Preferably the compositions will contain the active ingredient in an active but nontoxic amount selected from about 50 mg. to about 500 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The method in accordance with this invention comprises administering internally to a subject in need of uricosuric and hypouricemic activity the compound 2,3-dichloro-4-carboxyphenoxyacetic acid or a salt thereof, usually combined with a pharmaceutical carrier, in a nontoxic amount sufficient to produce said activity. The active ingredient will be administered preferably in a dosage unit, in an active, nontoxic quantity selected from about 50 mg. to about 500 mg. of the parent chemical of formula I. The route of administration may be orally or parenterally, the oral route being preferred. Advantageously equal doses will be administered two to four times daily with the daily dosage regimen being from about 100 mg. to about 1000 mg. When the method described above is carried out uricosuria and hypouricemia is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product. The following examples illustrate the preparation of the active ingredients employed herein and their incorporation into compositions of this invention.

EXAMPLE 1

A mixture of 33 g. (0.2 mole) of 2,3-dichlorophenol and 150 ml. of 50% sodium hydroxide was stirred and 50 ml. of water was added to dissolve the phenol more completely. Copper powder (0.4 g.) was added and the solution warmed. Carbon tetrachloride (65 g., 0.4 mole) was then added and the mixture refluxed for 48 hours.

After cooling the reaction mixture was poured onto ice and acidified with concentrated hydrochloric acid to congo red. The solution was chilled in an ice bath and the precipitate filtered.

The red clay-like solid was dried and suspended in 200 ml. of methylene chloride. After warming and stirring for 2 hours, the slurry was filtered. The precipitate was washed with a little methylene chloride and recrystallized from water after treatment with charcoal to give 2,3-dichloro-4-hydroxybenzoic acid: yield 17.8 g., m.p. 200° C.

2,3-dichloro-4-hydroxybenzoic acid (17 g.) was added to 100 ml. of a 3N aqueous solution of sodium hydroxide, followed by the addition of 9.45 g. of monochloroacetic acid. After refluxing for 2 hours, 5 g. of sodium hydroxide and 4.7 g. of monochloroacetic acid was added and the reflux continued for 2 hours.

The aqueous solution was acidified and the precipitate filtered and recrystallized in 50/50 dioxane/water to yield 2,3-dichloro-4-carboxyphenoxyacetic acid: yield 70%, m.p. greater than 250° C.

EXAMPLE 2

2,3-dichloro-4-hydroxybenzoic acid (4.8 g.) in 50 ml. of ethanol containing 2.65 g. of potassium hydroxide and 3.9 g. of potassium iodide was refluxed for 1 hour. Ethyl monochloroacetate (5.9 g.) was added and the mixture refluxed until the solution was neutral. Water (50 ml.) and 5 g. of potassium hydroxide was added and refluxing continued for 1½ hours. The reaction mixture was cooled, poured into water and acidified with hydrochloric acid to precipitate 2,3-dichloro-4-carboxyphenoxyacetic acid: yield 75%.

EXAMPLE 3

| Ingredients | Mg./Capsule |
|---|---|
| 2,3-dichloro-4-carboxyphenoxyacetic acid | 250 |
| Magnesium stearate | 2 |
| Lactose | 100 |

The above ingredients are screened through a #40 mesh screen, mixed and filled into #0 hear gelatin capsules. The capsules are administered to a subject twice daily.

What is claimed is:

1. A pharmaceutical composition in dosage unit form for producing uricosuria and hypouricemia comprising a pharmaceutical carrier and an amount sufficient to produce uricosuria and hypouricemia of the compound 2,3-dichloro-4-carboxyphenoxyacetic acid or an alkali metal salt of said acid.

2. The composition of claim 1 in which the active ingredient is in an amount of about 50 mg. to about 500 mg. per dosage unit.

3. The composition of claim 2 in which the active ingredient is in the form of the free acid.

4. A method of producing uricosuria and hypouricemia which comprises administering internally to a subject in need thereof a nontoxic amount sufficient to produce uricosuria and hypouricemia of the compound 2,3-dichloro-4-carboxyphenoxyacetic acid or an alkali metal salt of said acid.

5. The method of claim 4 in which the active ingredient is administered with a pharmaceutical carrier in dosage unit form.

6. The method of claim 5 in which the administration is orally.

7. The method of claim 4 in which a daily dosage of from about 100 mg. to about 1000 mg. of active ingredient is administered.

8. The method of claim 5 in which dosage units containing from about 50 mg. to about 500 mg. of active ingredient are administered from 2 to 4 times daily.

9. The method of claim 4 in which the active ingredient is in the form of the free acid.

* * * * *